United States Patent
Ratna et al.

(10) Patent No.: US 8,831,386 B2
(45) Date of Patent: Sep. 9, 2014

(54) METAMATERIAL OPTICAL ELEMENTS SELF-ASSEMBLED ON PROTEIN SCAFFOLDS

(75) Inventors: Banahalli R. Ratna, Alexandria, VA (US); Amy S. Blum, Montreal (CA); Carissa M. Soto, Alexandria, VA (US); Michael A. Bruckman, Cleveland Heights, OH (US); Jinny Lin Liu, Ellicott, MD (US); Ronald W. Rendell, Washington, DC (US); James Peter Long, Accokeek, MD (US); Ronald J. Tonucci, Waldorf, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 337 days.

(21) Appl. No.: 13/349,189

(22) Filed: Jan. 12, 2012

(65) Prior Publication Data
US 2013/0181171 A1 Jul. 18, 2013

(51) Int. Cl.
*G02F 1/061* (2006.01)
*G02B 6/00* (2006.01)

(52) U.S. Cl.
USPC .............. 385/12; 385/131; 385/141; 359/244

(58) Field of Classification Search
USPC ............ 252/500, 512–514; 385/12, 129, 131, 385/141; 435/5; 359/244; 257/421
See application file for complete search history.

(56) References Cited

U.S. PATENT DOCUMENTS

| 7,646,524 | B2 | 1/2010 | Tonucci | |
|---|---|---|---|---|
| 7,683,444 | B2 | 3/2010 | Tonucci | |
| 7,808,722 | B2 | 10/2010 | Tonucci | |
| 8,019,555 | B1 * | 9/2011 | Ratna et al. | ............... 702/22 |

FOREIGN PATENT DOCUMENTS

CN  102899346  * 9/2012

OTHER PUBLICATIONS

Li et al "The development and application of new crystallization method for tobacco mosai virus coat protein", Virology Journal 2012, 9:279 12 pages.*
Heddle "Protein cages, rings and tubes: useful components of future nanodevices", Nanotechnology, Science and Applications 2008; 1 67-78.*
Kadri et al "Engineered tobacco mosaic virus . . . ", Virus Research 157(2011) 35-46.*
Lee et al "Improved metal cluster deposition on a genetically engineered tobacco mosaic virus template", Nantechnology 16 (2005) S435-441.*
Bruckman et al "Role of hexahistidine in directed nanoassemblies of tabacco mosaic virus coat protein", ACSNano 5(3), 1606-1616 (published online Feb. 25, 2011).*
Alù, A.; Engheta, N. Phys. Rev. B 2008, 78, 085112.

(Continued)

*Primary Examiner* — Mark Kopec
(74) *Attorney, Agent, or Firm* — US Naval Research Laboratory; Roy Roberts

(57) ABSTRACT

Protein scaffolds from tobacco mosaic virus coat protein modified to incorporate polyhistidine can bind to a metal or a dye while having improved self-assembly characteristics. The scaffold can take the form of tubes or disks, and can further be formed into dual plasmonic ring resonators. Such self-assembled structures provide useful optical properties.

16 Claims, 12 Drawing Sheets
(1 of 12 Drawing Sheet(s) Filed in Color)

(56) References Cited

OTHER PUBLICATIONS

Blum, A. S.; Soto, C. M.; Wilson, C. D.; Brower, T. L.; Pollack, S. K.; Schull, T. L.; Chatterji, A.; Lin, T.; Johnson, J. E.; Amsinck, C.; Franzon, P. D.; Shashidhar, R.; Ratna, B. R. Small 2005, 1, 702.

Bruckman, M. A.; Kaur, G.; Lee, L. A.; Xie, F.; Sepulveda, J.; Breitenkamp, R.; Zhang, X.; Joralemon, M.; Russell, T. s. P.; Emrick, T.; Wang, Q. ChemBioChem 2008, 9, 519-523.

Culver, J. N.; Dawson, W. O.; Plonk, K.; Stubbs, G. Virology 1995, 206, 724-730.

Dedeo, M. T.; Duderstadt, K. E.; Berger, J. M.; Francis, M. B. Nano Lett. 2010, 10, 181-186.

Dujardin, E.; Peet, C.; Stubbs, G.; Culver, J. N.; Mann, S. Nano Lett. 2003, 3, 413-417.

Klug, A. Philos. Trans. R. Soc. Lond. B 1999, 354, 531-535.

Li, K.; Nguyen, H. G.; Lu, X. B.; Wang, Q. Analyst 2010, 135, 21-27.

Nam, K. T.; Peelle, B. R.; Lee, S.-W.; Belcher, A. M. Nano Lett. 2004, 4, 23-27.

Niu, Z. W.; Bruckman, M.; Kotakadi, V. S.; He, J. B.; Emrick, T.; Russell, T. P.; Yang, L.; Wang, Q. Chem. Commun. 2006, 3019-3021.

Niu, Z.; Bruckman, M. A.; Li, S.; Lee, L. A.; Lee, B.; Pingali, S. V.; Thiyagarajan, P.; Wang, Q. Langmuir 2007, 23, 6719-6724.

Niu, Z.; Liu, J.; Lee, L. A.; Bruckman, M.; Zhao, D.; Koley, G.; Wang, Q. Nano Lett. 2007, 7, 3729-3733.

Pendry, J. B.; Holden, A. J.; Robbins, D. J.; Stewart, W. J. IEEE Trans. Microwave Theory Tech. 1999, 47, 2075.

Royston, E.; Brown, A. D.; Harris, M. T.; Culver, J. N. J. Colloid Interface Sci. 2009, 332, 402-407.

Royston, E.; Ghosh, A.; Kofinas, P.; Harris, M. T.; Culver, J. N. Langmuir 2008, 24, 906-912.

Schlick, T. L.; Ding, Z.; Kovacs, E. W.; Francis, M. B. J. Am. Chem. Soc. 2005, 127, 3718-3723.

Soto, C. M.; Ratna, B. R. Curr Opin Biotech 2010, 21, 1-13.

Yi, H.; Nisar, S.; Lee, S. Y.; Powers, M. A.; Bentley, W. E.; Payne, G. F.; Ghodssi, R.; Rubloff, G. W.; Harris, M. T.; Culver, J. N. Nano Lett. 2005, 5, 1931-1936.

\* cited by examiner

METAMATERIAL OPTICAL ELEMENTS SELF-ASSEMBLED ON PROTEIN SCAFFOLDS

BACKGROUND

Material having electric permittivity and magnetic permeability that are simultaneously negative at certain frequencies have a negative index of refraction for these frequencies. Plasmonic ring resonators (PRRs), which include split ring resonators (SRRs), have been used to create materials having a negative index of refraction, also termed negative index materials (NIMs). See, for example, commonly-owned U.S. Pat. Nos. 7,646,524, 7,683,444, and 7,808,722 as well as *Fast Light, Slow Light and Left-Handed Light*, P. W. Milonni, Institute of Physics Publishing (2005), each of which is incorporated herein by reference in its entirety.

NIMs have several applications, for example in the production of superlenses, which overcome the diffraction limit by enhancing and recovering the evanescent waves emitted by an object to allow resolution of features much smaller than the incident wave. Although NIMs have been produced in the microwave frequencies, it remains a challenge to produce NIMs that operate in the visible/near infrared spectrum due to the required size of the resonant structures. Moreover, it has been proposed that, in theory, a ring of metallic nanoparticles can create magnetic oscillations at optical frequencies by the formation of displacement currents excited from an optical source. Such optically active structures can produce a permeability value different from unity at optical and near infrared frequencies.

The various structures necessary for realizing such optical phenomena require nanoscopic control of structural details. Nano-lithographic techniques to create such structures with features in the range of 10 or 10s of nanometers are time consuming, expensive and suffer from a lack of registration over extended length scales. Thus, a need exists for fabrication of high resolution nanoscale metamaterial structures.

BRIEF SUMMARY

Tobacco mosaic virus coat protein (TMV-CP) can be used as a nanosized scaffold for building PRRs and other nanostructured circuit elements (NSE) with nanoscale features.

In one embodiment, a protein scaffold comprises a tobacco mosaic virus coat protein genetically modified to incorporate polyhistidine and in the form of one or more protein disks of 18 nm diameter.

In another embodiment, a protein scaffold comprises a tobacco mosaic virus coat protein disk of 18 nm diameter and bound to a metal in the form of a metal-decorated disk of 20 to 30 nm diameter.

In a further embodiment, a method of obtaining metal nanoparticle decorated disks comprises assembling a genetically modified tobacco mosaic virus coat protein incorporating polyhistidine into disks, and coating the disks with metal nanoparticles to obtain metal nanoparticle decorated disks of 20 to 30 nm diameter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows His-TMV-CP and WT-TMV-CP control samples in 400 mM buffer after 4 days at 4° C. at various pHs.

FIG. 6A shows 139Cys-His-TMV-CP after reaction and purification. FIG. 6B shows an atomic force microscopy (AFM) image of purified 139Cys-His-TMV-CP.

FIG. 8A shows His-TMV-CP disk-Au complexes. FIG. 8B uses the same image as FIG. 8A but with superimposed schematic images of the size and shape of the expected 20 nm disks.

FIG. 9A shows His-TMV-CP rods that were assembled in solution at 400 mM buffer concentration pH 5.0 and stained with uranyl acetate for visualization purposes. FIG. 9B shows His-TMV-CP rods after reaction with Ni-NTA-Nanogold and the sample was not stained.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials that are similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the term "plasmonic ring resonator" refers to a plasmonic waveguide in the shape of a ring and comprising closely spaced metallic material (for example, gold or silver). Although the metallic material is closely spaced along the ring, one or more small gaps may exist (i.e., the ring may be optionally be split and/or disordered, for example to form a split ring resonator). A plasmonic ring resonator generally has a diameter of no greater than 100 nm, with certain embodiments of plasmonic ring resonators having diameters of about 30, 29, 28, 27, 26, 25, 24, 23, 22, 21, or 20 nm.

As used herein, the term "tobacco mosaic virus coat protein" (TMV-CP) includes the wild-type protein as well chemically and/or genetically modified variants thereof.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Description

Tobacco mosaic virus coat protein (TMV-CP) can be used as a nanosized scaffold for nanoscale structures. Seventeen individuals coat proteins assemble to form a single 18 nm disk or ring. See FIG. 1. These disks normally stack around the TMV RNA genome to form a tube that is 300 nm long and 18 nm in diameter. See, e.g., Bruckman et al., ACS Nano, Vol. 5, No. 3, pp. 1606-1616 (2011) and O. K. Zahr and A. S. Blum, "Solution Phase Gold Nanorings on a Viral Protein Template," Nano Lett., web publication dated Dec. 26, 2011, each of which is incorporated herein by reference.

Figure 1:
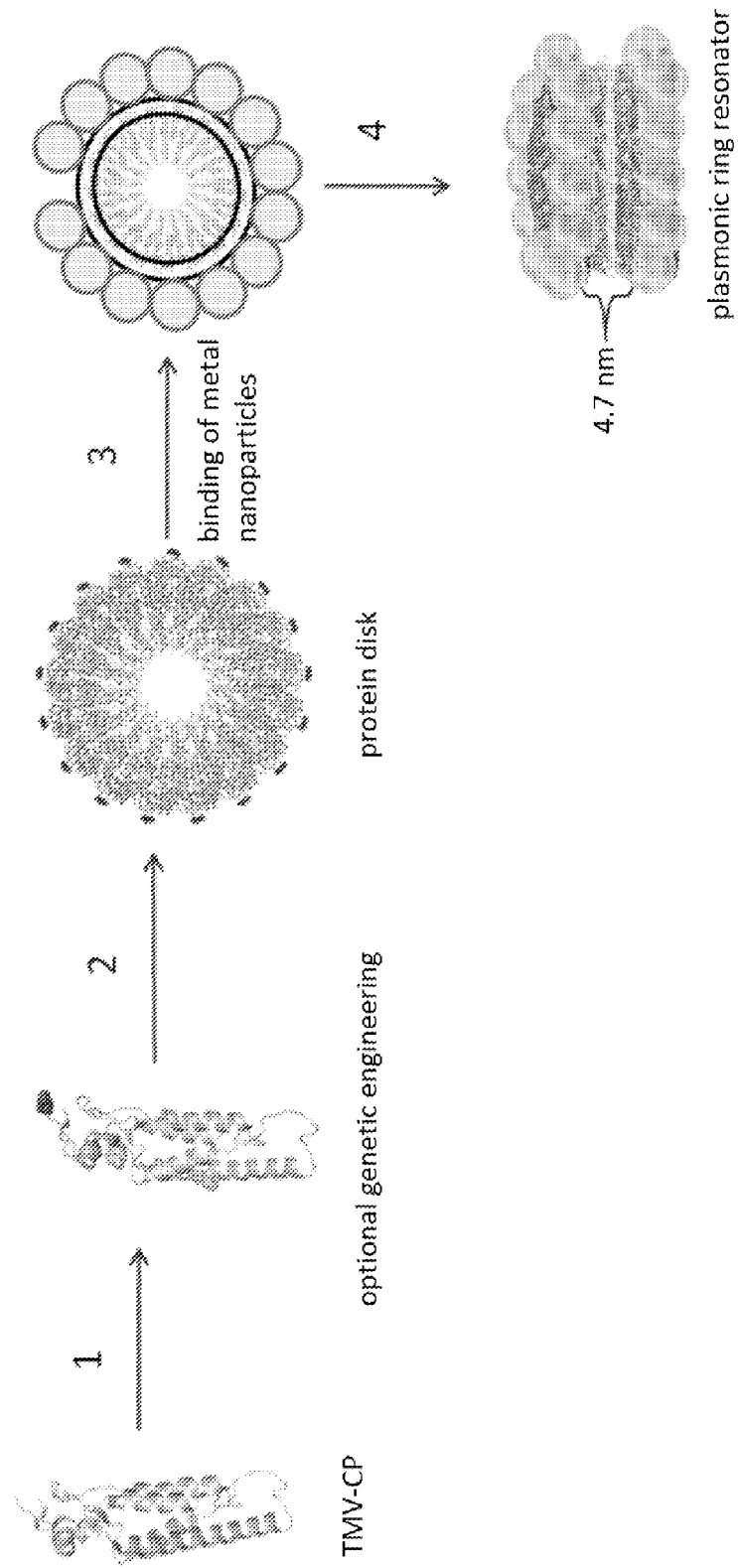
FIG. 1 is a schematic of how illustrative embodiments of the plasmonic ring resonators were created by self-assembly. Based on the protein structure of tobacco mosaic virus coat protein (TMV-CP) genetic engineering was performed to generate proteins with available chemical handles for nanoparticle binding (1). After protein production the proteins self-assemble in solution to form disk-like structures of about 18 nm in diameter (2). Disks are mixed with nanoparticles (3) that carry proper chemistries for binding. Resultant disks-nanoparticle complexes form plasmonic ring resonators (4).

The TMV coat protein can be genetically modified as described herein to incorporate polyhistidine, which (1) desirably improves the stability of the disk form of the protein, and (2) provides a binding site for metals, so that when assembled in a disk, 17 metal-binding sites are present. The present inventors have used polyhistidine-modified TMV coat protein as a protein scaffold to form metal-decorated disks of 20 to 30 nm diameter, which are expected to serve as plasmonic ring resonators and otherwise provide utility in building nanostructured circuit elements (NSE) with nanoscale features. A schematic illustrating an exemplary embodiment is seen in FIG. 1. Although genetic engineering to incorporate polyhistidine is a preferred embodiment, wild-type coat protein may be employed, for example with one or more chemical modifications. For example, wild-type protein may be chemically modified to include polyhistidine and/or other functional elements such as a peptide linker.

The wild-type TMV coat protein (WT-TMV-CP) can be isolated as three major assembled components in the absence of the TMV genome: protein A (a dynamic equilibrium between monomers, trimers, and pentamers of WT-TMV-CP), disks consisting of 34 monomers (also known as the 20S structure), and helical rods of various lengths. WT-TMV-CP assemblies in solution can be controlled to favor protein A, disks, or rods depending on the pH and ionic strength. Previous work involving modification of the WT-TMV-CP either through genetic engineering or chemical modifications did not significantly change the equilibrium conditions between the various assemblies. However, the present inventors have found that histidine-modified TMV coat protein was found to significantly affect the self-assembly as compared to the wild-type coat protein, a fact that can be exploited to prepare nanostructured circuit elements (NSEs) under a wider variety of conditions. The incorporated His tag further provides a chemical handle to allow for binding of certain nanoparticles. This allowed the construction of Au-disk structures of about 30 nm in diameter which are expected to produce negative index materials as a component of a three dimensional arrangement.

Previous work on nano-scale structures from TMV-CP did not incorporate the polyhistidine tag, which as described herein was surprisingly found to extend the ability of disk-like structure to exist a broader range of conditions. Such stabilization of the disk-like structure is critical for the construction of the plasmonic ring resonator. After allowing for the metal decorating the 18 nm protein disk, the plasmonic ring resonators are preferably from 20 nm to 30 nm in diameter for obtaining the desired magnetic resonances at optical wavelengths.

As NSEs can be designed and fabricated in the form of nanoscale plasmonic ring resonators, nanoscale coupled plasmonic ring resonators and nanoscale elements containing clusters of metal, insulator and/or semiconductor nanoparticles functional at optical or near infrared frequencies. Optical gain, in the function of the nanostructured circuit elements, can also be introduced by incorporation of dye or other materials that can be pumped separately or as part of a resonant scattering process.

Electromagnetic Response of TMV Nanoparticle Arrays

The electromagnetic response of TMV nanoparticle arrays for both TMV disks and TMV nanorods was evaluated by numerical modeling.

Modeling was performed by numerical simulation using the finite-element code, COMSOL Multiphysics. This code allows construction of the 3-dimensional geometries of the nanoparticles and attachment of these along the virus structure to form arrays of arbitrary design. Material properties are incorporated in terms of the frequency dependent dielectric functions of the metals comprising the nanoparticles and surrounding dielectrics. The electromagnetic fields corresponding to plasmonic excitations in these configurations are found by solving the governing electromagnetic equations with appropriate boundary conditions. The characteristics of the spectra of the localized and propagating plasmon modes can be studied for their dependences on the geometry, configuration and material properties of the nanoparticle structures as well as their method of excitation.

The calculated near-fields of TMV disks indicated that magnetic resonances in the visible are found to be excited in response to an incident plane wave polarized with the applied magnetic field perpendicular to the plane of the disk. The magnetic resonance is found to be governed primarily by loops of electric displacement current around the ring of particles. A variety of particle ring designs were studied which are compatible with the attachment of 3-5 nm Au and Ag nanoparticles on the TMV disks. These can be viewed as distributions of individual particles and dimers placed at different spacings around the circumference of the disk as shown by the three examples (i), (ii), and (iii) in FIG. 2A. The wavelengths of the resonances are found to be close to that of an isolated nanoparticle dimer (shown by the thinner of the solid lines in FIG. 2A) but red-shifted and enhanced due to the plasmonic coupling of closely-spaced particles (shown as "coupled modes" in the figure) or due to ohmic contact between the particles (shown as "contact modes" in the figure). The magnetic resonance response for the various arrays is closely grouped into these two types of modes but differ in detail due to the variety of spacings.

Figure 2A:
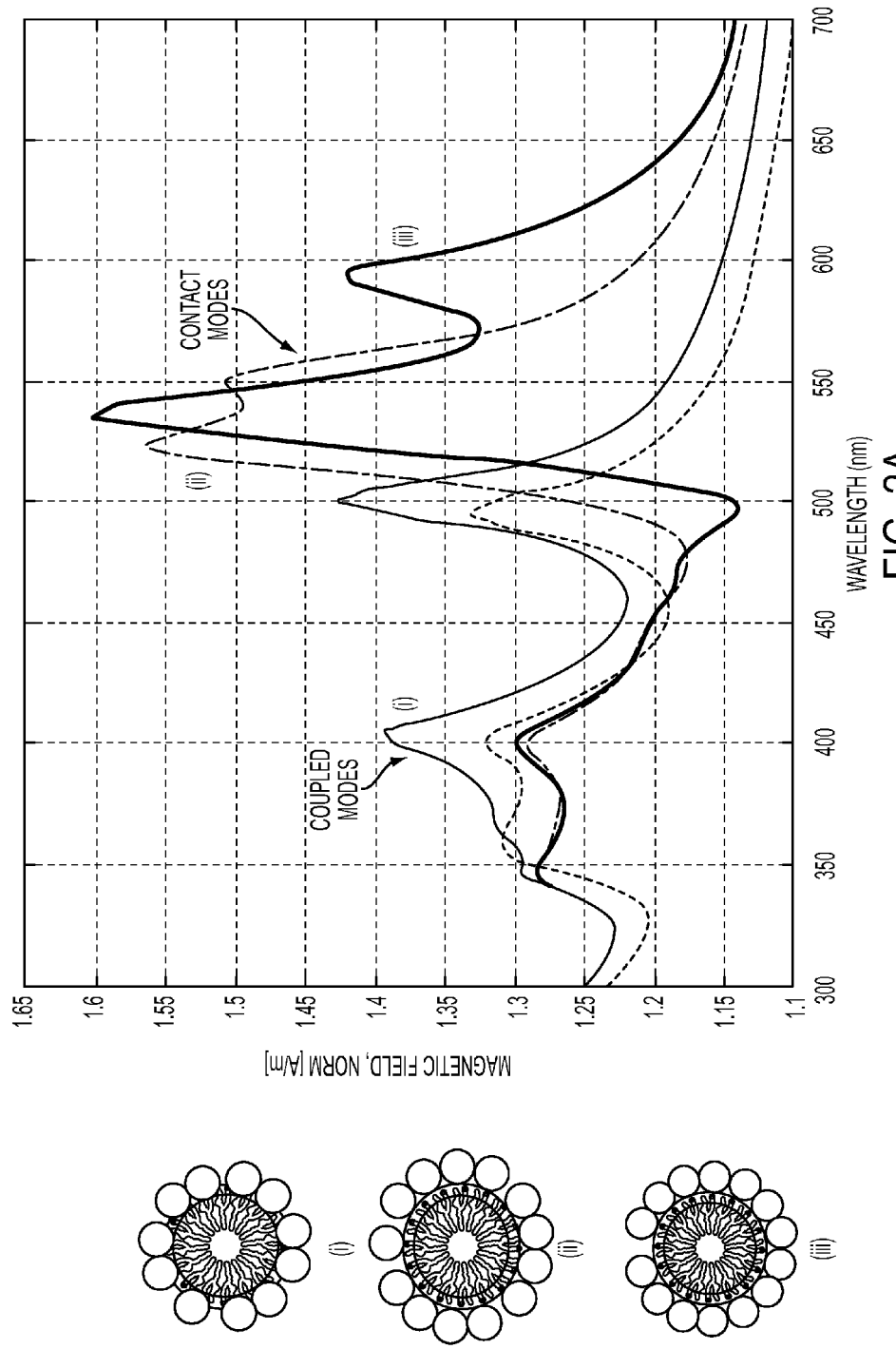
FIG. 2A illustrates modeled results of the magnetic near-field resonance response in the visible for nanoparticle-array TMV disk designs in response to an incident plane-wave with magnetic field perpendicular to the disk plane. The resonances are near those of an isolated dimer (lighter weight lines, solid and with uniform dashes) but enhanced and shifted due to plasmonic coupling and contact coupling.
Figure 2B:
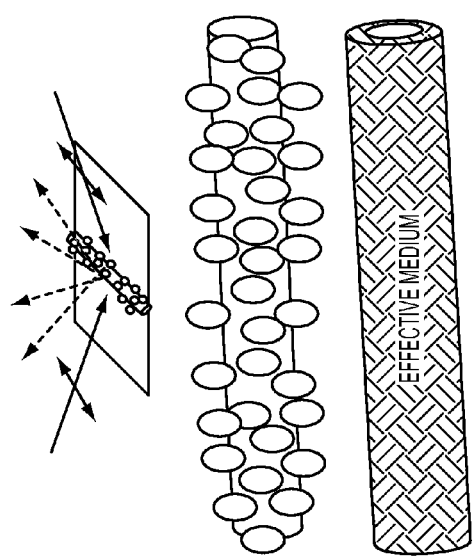
FIG. 2B shows calculated far-field scattering cross-section in the visible of a 500 nm TMV rod coated with an effective-medium representing a random nanoparticle coating and lying on an oxidized Si substrate to an incident plane wave polarized along the length of the rod. The scattering response corresponds both to surface plasmons localized on the TMV rod and to plasmons due to the contact of the TMV rod with the substrate.
Figure 2B:
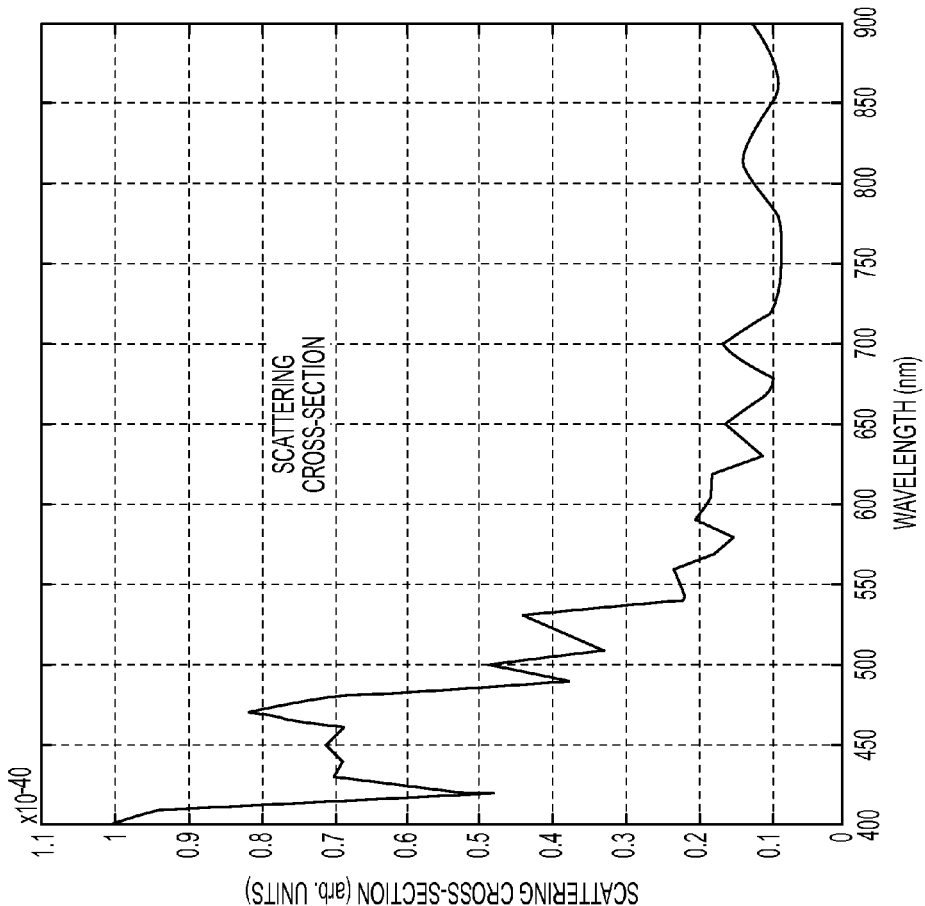

FIG. 2B shows the scattering cross-section in the visible obtained from the calculated far-fields of a nanoparticle-coated 500 nm long TMV nanorod in response to an incident plane wave, using modeled data. This was incident at 11 degrees from the surface with electric field polarized along the length of the rod and the scattered far-fields were collected within a half-angle cone of 64 degrees corresponding to the conditions of dark-field measurements. The nanorod lies on a substrate consisting of 100 nm $SiO_2$ on Si. The random distribution of 6 nm Au nanoparticles on the surface of the rod was represented by an Au/Air Bruggeman effective medium of spherical inclusions. The scattered response of the nanoparticle-coated TMV rod has contributions both due to the localized surface plasmons of the nanoparticles and due to plasmonic modes due to the contact of the TMV rod with the substrate.

Figure 2C:
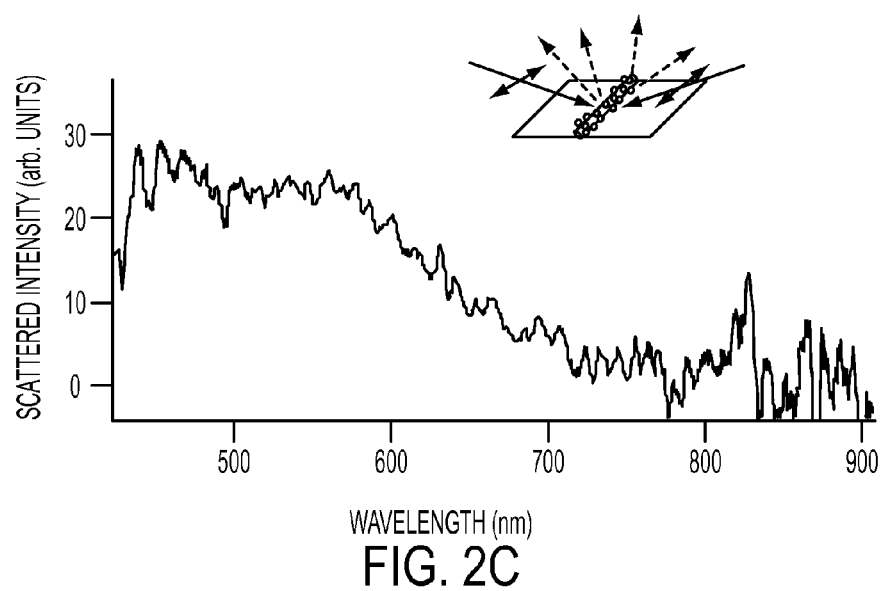
FIG. 2C shows an experimental spectrum obtained from a 500 nm long TMV rod decorated with 6 nm diameter Au NPs.

FIG. 2C shows a single particle scattering spectrum obtained with actual experimental data for a 500 nm long TMV rod decorated with 6 nm diameter Au NPs. The incident light was polarized in the plane and directed in beams perpendicular to the rod.

Figure 2D:
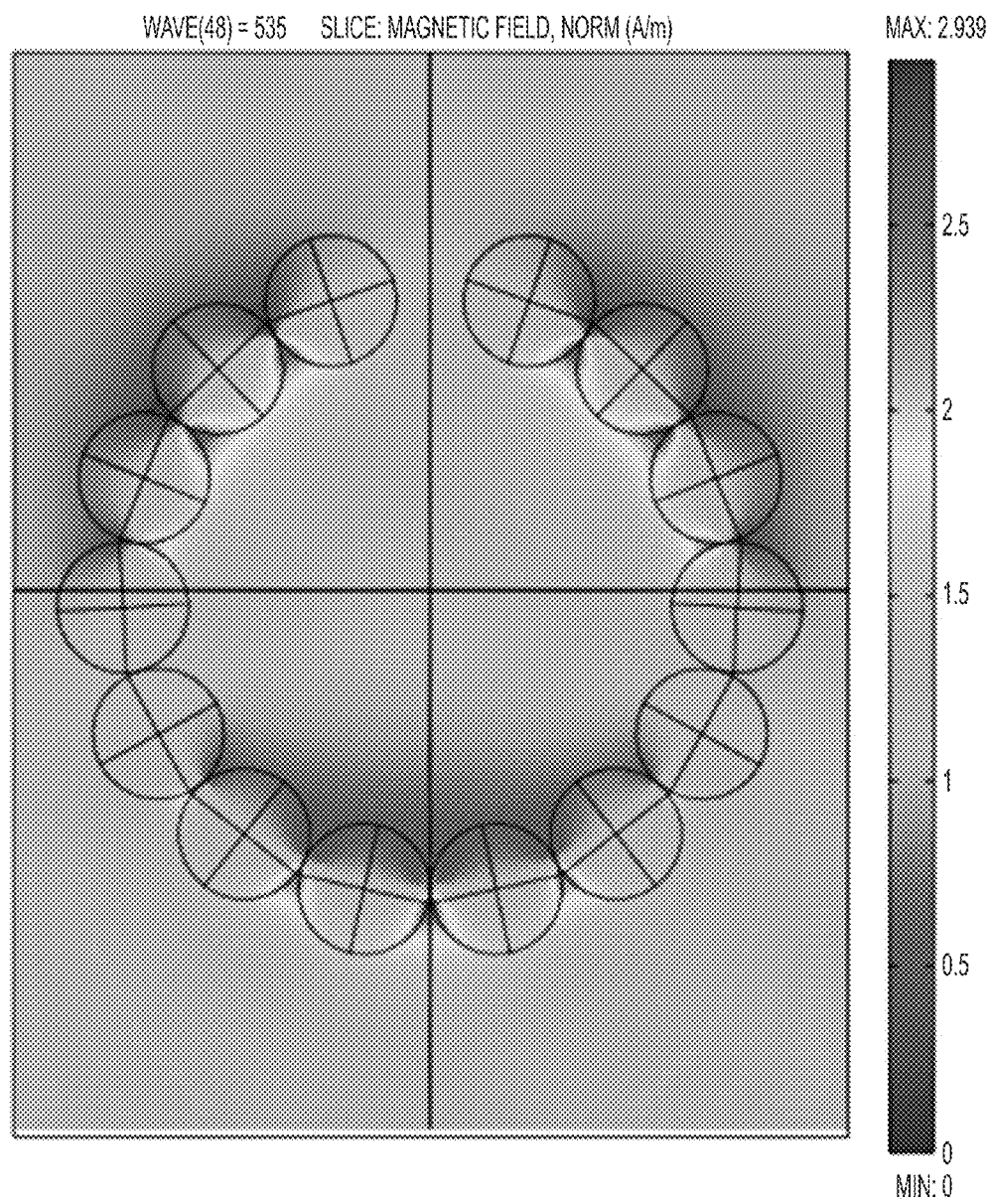
FIG. 2D shows modeled results of the magnetic near-field resonance response in the visible for nanoparticle-array TMV disk designs in response to an incident plane-wave with magnetic field perpendicular to the disk plane, based on the ring configuration depicted in arrangement (iii) of FIG. 2A.

FIG. 2D shows modeled results of the magnetic near-field resonance response in the visible for nanoparticle-array TMV disk designs in response to an incident plane-wave with magnetic field perpendicular to the disk plane, based on the ring configuration depicted in arrangement (iii) of FIG. 2A.

Production of His-TMV-CP

The primers TMVCP F1 (SEQ ID NO: 1) and His-TMV-CP R1 (SEQ ID NO: 2) were used in a PCR reaction using a wild-type TMV coat protein gene product 6 ("gp6") template (comprising SEQ ID NO: 3). Conditions for amplification were 35 cycles of 95° C. for 30 sec, 55° C. for 30 sec, and 68° C. for 30 sec. The resulting amplified fragments were then digested with NdeI and NcoI and were subsequently inserted into pET20b vectors DNA using T4 DNA ligase. The ligation mixture was then electroporated into XL1 Blue and plated on LB plates supplemented with 100 µg/mL of ampicillin for overnight incubation at 37° C. Plasmid DNA was then isolated from three potential positive clones grown on the plates and were sent out for DNA sequencing. The sequence confirmed clone, His-TMV-CP-2 (SEQ ID NO: 4), containing 6×His at C-terminus, was then sub-cloned to the expression host, *E. coli* strain Rosetta2(DE3)pLysS for protein expression and purification using conventional techniques—details can be found in Bruckman et al., ACS Nano, Vol. 5, No. 3, pp. 1606-1616 (2011). The resulting His-TMV-CP protein was observed at 18.5 kDa on a polyacrylamide gel.

Although this example created a hexahistidine-tagged protein, one of ordinary skill in the art may prepare a protein having an alternate number of histidines in the polyhistidine tag, for example 4, 5, 6, 7, 8, 9, 10, 11, or 12 histidines. For example, genetic engineering might be employed to adjust the gap between two metal-decorated protein disks, which is normally 4.7 nm (see FIG. 1). Polyhistidine could be added at the N terminal end of the protein, or elsewhere, instead of the C terminal end as was done in the example. Other modifications to TMV coat protein are contemplated: for example, a peptide linker to enlarge the CP is expected to increase the diameter of the resulting protein disk—such a peptide might be added at the C terminal end, for example before or after a polyhistidine tag. Such modifications may be performed genetically and/or chemically.

Assembly of His-TMV-CP Disks and Rods

His-TMV-CP stock solution at 1.0 mg/mL was centrifuged for 15 min at 4° C. at 9,300 g. The resulting pellet was recovered and dissolved in minimal 100 mM potassium hydroxide (KOH) added in 20 µL increments. The suspended pellet was incubated at 4° C. for two hours. Protein concentration was determined by using absorbance values of the peak at 278 nm and previously reported extinction coefficient ($\in$=1.3 mL $mg^{-1}$ $cm^{-1}$). The concentration of His-TMV-CP was set to 1.7 mg/ml and dialyzed against 10 mM or 100 mM potassium/sodium phosphate at pH 8.5 at 4° C. in a Slide-A-Lyzer MINI dialysis unit (10 kDa MWCO). At this stage the protein is refolded into the protein A form. Protein samples at pH 8.5 were dialyzed for 24 hr at 4° C. against buffers at pH values: 8.0, 7.0 or 6.0 at the desired ionic strength.

Figure 3:
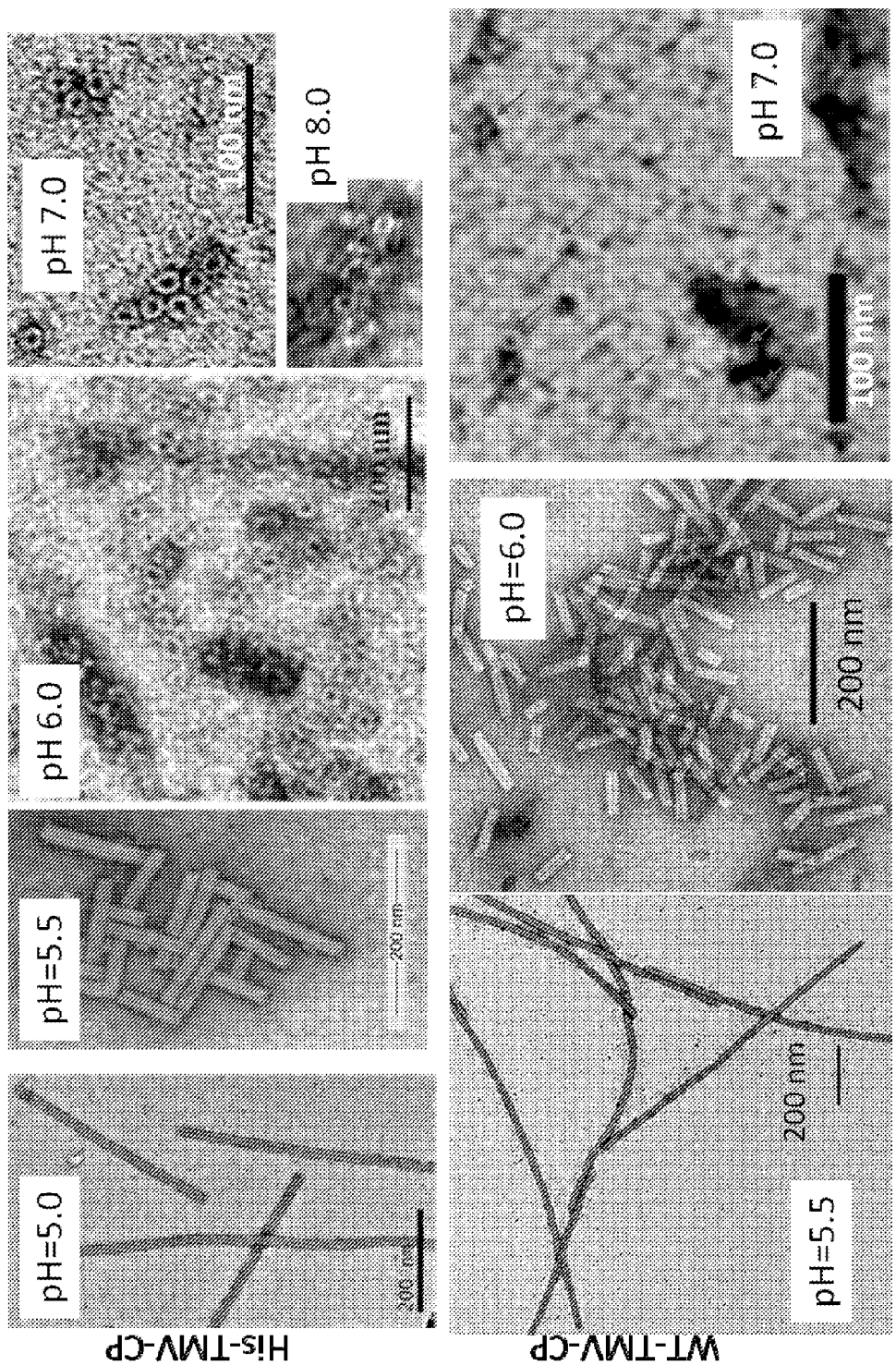
FIG. 3 contains micrographs of His-TMV-CP and WT-TMV-CP samples in 100 mM buffer after 4 days at 4° C. at various pHs.

For the assembly of rods a protein solution in 10/100 mM phosphate buffer pH 8.5 is dialyzed against 10 or 100 mM sodium acetate buffer pH 5.5. FIG. 3 contains micrographs of His-TMV-CP and WT-TMV-CP samples in 100 mM buffer after 4 days at 4° C. at various pHs. As pH increases, the dominant structure changes from rods to disks. This transition occurs at a lower pH for His-TMV-CP (pH 6.0) than for WT-TMV-CP (pH 7.0). In addition, disks are still seen at pH 8.0 for His-TMV-CP, while WT-TMV-CP under the same conditions is in protein A form (arrows in FIG. 3).

Figure 4:
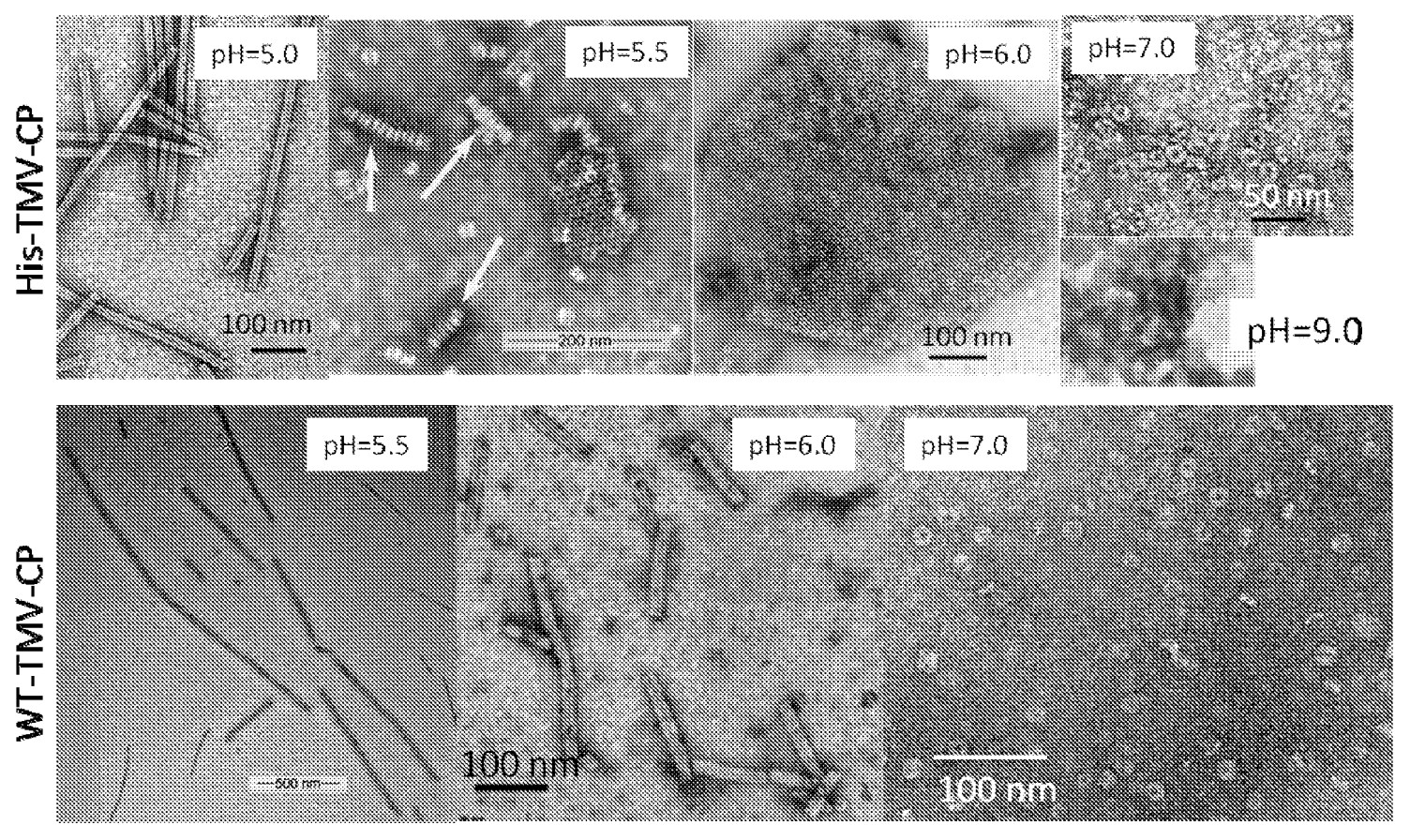

For higher ionic strengths studies protein in 100 mM phosphate buffer pH 8.5 is dialyzed for 24 hr at 4° C. against 400 mM phosphate buffer at pH values: 8.0, 7.0, 6.0 or 400 mM sodium acetate pH 5.5, as seen in FIG. 4 showing His-TMV-CP and WT-TMV-CP samples in 400 mM buffer after 4 days at 4° C. at various pHs. As pH increases, the dominant structure changes from rods to disks. This transition occurs at a lower pH for His-TMV-CP (pH 5.5) than for WT-TMV-CP (pH 7.0). His-TMV-CP shows some additional extended structures. At pH 5.5, there are some stacked disks (indicated by white arrows) and some small hexagonally packed islands. At pH 6.0, hexagonally packed islands are the dominant structure and are much larger in size. At pH 9.0, both TMV-CP proteins are in protein A form.

The image in the top row of FIG. 4 at pH 6 shows a sheet of material that was obtained with His-TMV-CP but could not be obtained with WT-TMV-CP, thus demonstrating the surprising and unexpected improved protein structure obtained when polyhistidine incorporated.

Assessment of Available Chemistries: Amines and Thiols

Figure 5:
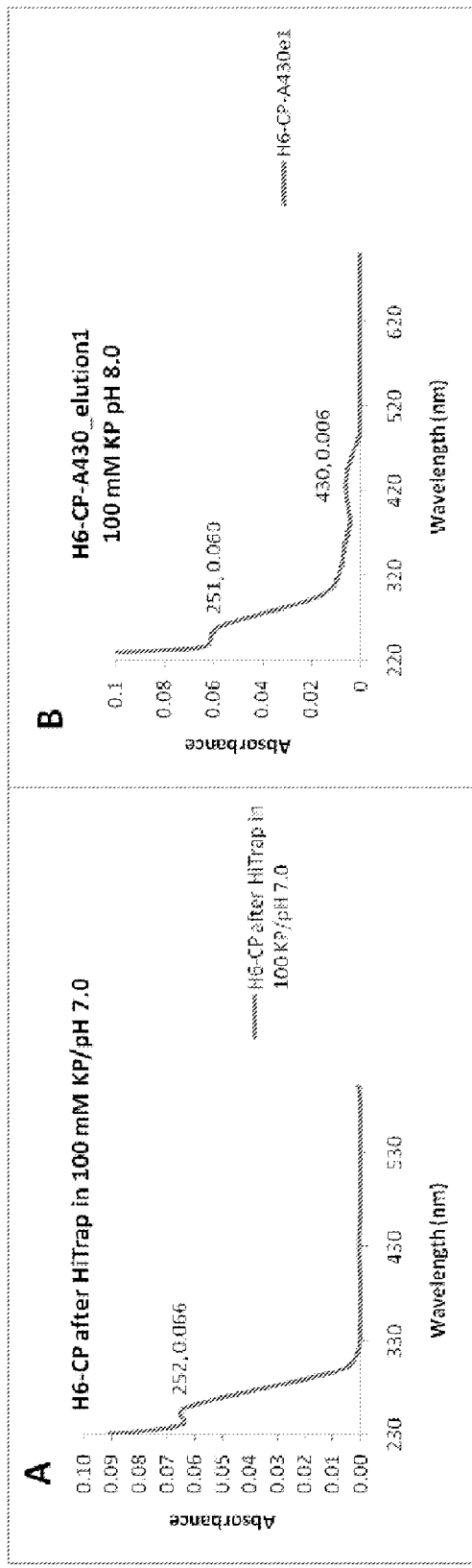
FIGS. 5A and 5B show His-TMV-CP before and after conjugation with a dye having an adsorption peak at 430 nm.

Purified His-TMV-CP (FIG. 5A) was mixed with NHS ester AlexaFluor430 dye and mixed overnight at room temperature, followed by purification with size exclusion chromatography. This resulted in the appearance of a new peak at 430 nm, indicating that the dye had attached to available reactive amines on the His-TMV-CP, as seen in FIG. 5B.

Figure 6:
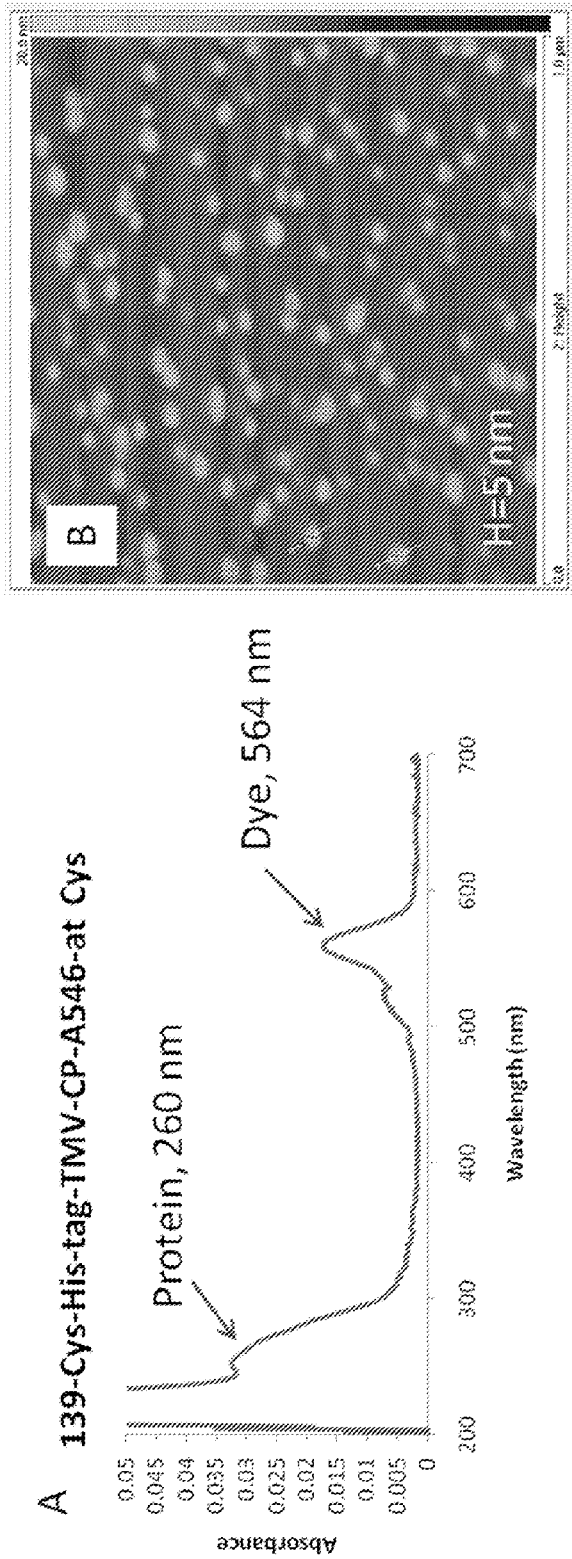
FIGS. 6A and 6B show reactivity of AlexaFluor546 maleimide dye towards solvent-accessible thiols present in 139Cys-His-TMV-CP.

The protein 139Cys-TMV-CP (SEQ ID No: 5) was constructed, comprising a cysteine amino acid which was incorporated by genetic engineering at position 139 of the protein, along with the histidine tags of the His-TMV-CP construct. After expression and purification, the protein was reacted with AlexaFluor 546 maleimide, resulting in a new peak at 546 nm, showing that the dye successfully attached, as seen in FIG. 6A. FIG. 6B shows an atomic force microscopy (AFM) image of purified 139Cys-His-TMV-CP where assembled disks can be seen. The self-assembly properties of the protein into disk-like structure was not been affected by the reaction and purification conditions. FIG. 6B show an atomic force microscopy (AFM) image of assembled disks of purified 139Cys-His-TMV-CP bound to the AlexaFluor 546 maleimide.

Reactivity with Gold Nanoparticles

Figure 7:
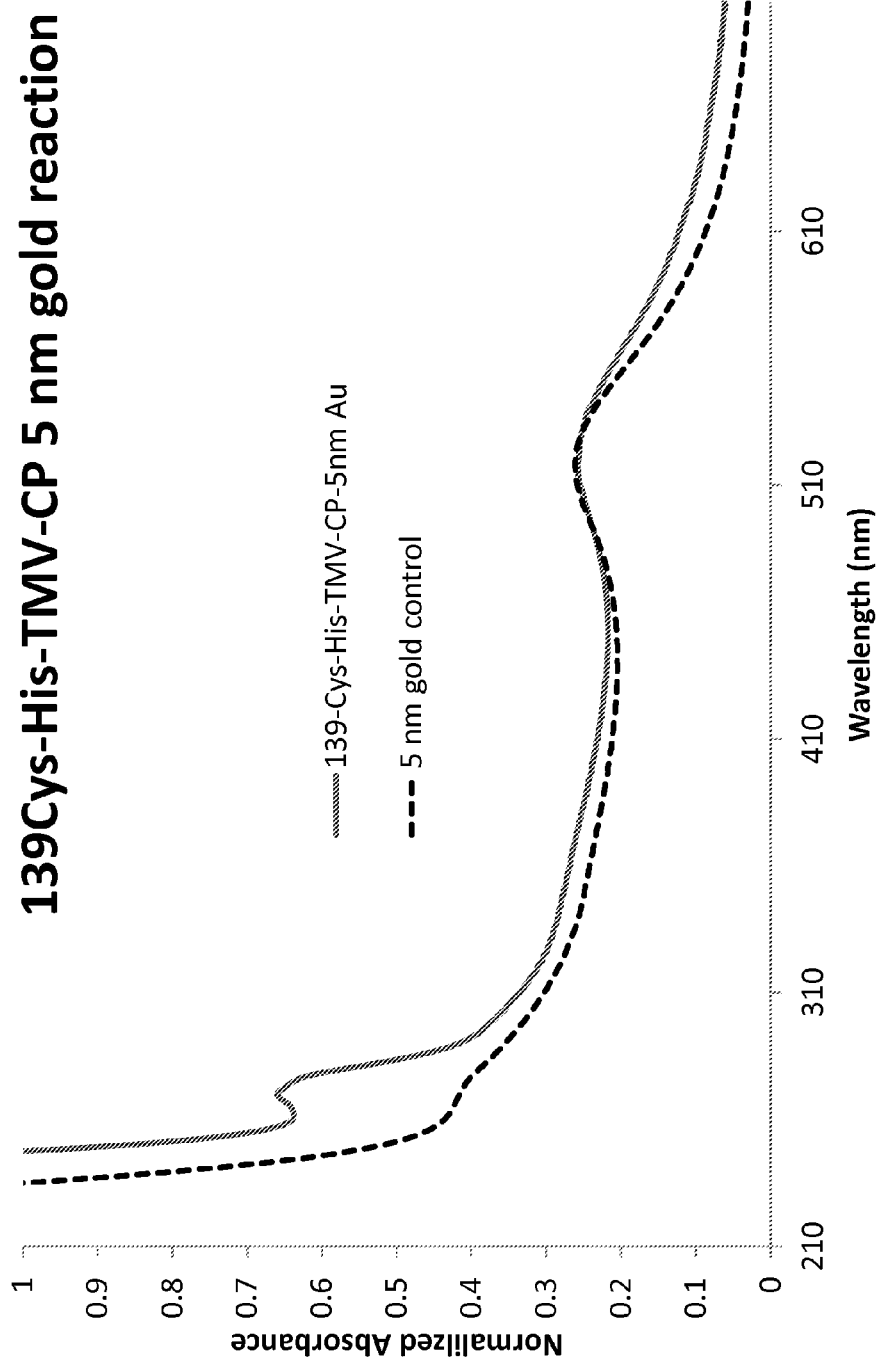
FIG. 7 shows UV-Vis of samples recovered from 1% low melting agarose gel. 139-Cys-TMV-CP gold complex was recovered from the gel using electroelution (solid line). Buffer containing sample was concentrated and analyzed by UV-Vis spectroscopy. Similar procedure was done on the free gold band and used as a control (dashed line). Peak at 530 nm correspond to the plasmon resonance of 5 nm gold and the peak at 278 nm to the protein peak. Data was normalized relative to absorbance at 530 nm.

Samples of 139-Cys-His-TMV-CP were mixed with 5 nm gold and left to react for 5 days at room temperature. The mixture was concentrated by using a Centricon unit with a molecular weight cut-off of 100 kDa and loaded in a 1% low melting agarose. A protein-gold band appeared in the expected position on the gel, and the 139-Cys-TMV-CP gold complex was recovered from the gel using electroelution. Buffer containing sample was concentrated and analyzed by UV-Vis spectroscopy, as seen in FIG. 7.

Reactivity with Ni-NTA-Nanogold

Fifty microliters of His-TMV-CP rods or disks (assembled as described above, with 1.0 mg/ml, 400 mM potassium phosphate buffer pH=6.0 for disks, 400 mM acetate pH=5.0 for rods) were mixed with 50 μL Ni-NTA (nitrilotriacetic acid) coated Au nanoparticles (5 nm, 0.5 μM, from Nanoprobes in Yaphank, N.Y.) for 30 minutes at room temperature prior to spotting the sample on a TEM grid (holey carbon coating, from SPI Supplies). No staining was performed for TEM grid preparation of gold containing samples. Dark spots in TEM images correspond to 5 nm gold. Free gold was not removed from reaction mix prior to TEM imaging. The best mode found for preparing disk-Au complexes was found to be when the disks were assembled at 400 mM buffer concentration at pH 6.0 and the protein to gold ratio was 1:5 (v:v) for the reaction with Ni-NTA-Nanogold, with results seen in FIG. 8. The best rod-Au assemblies were obtained when the rods were assembled at 400 mM buffer concentration pH 5.0, followed by reaction with Ni-NTA-Nanogold at a protein to Au ratio of 1:1 (v:v), results seen in FIG. 9.

Figure 8:
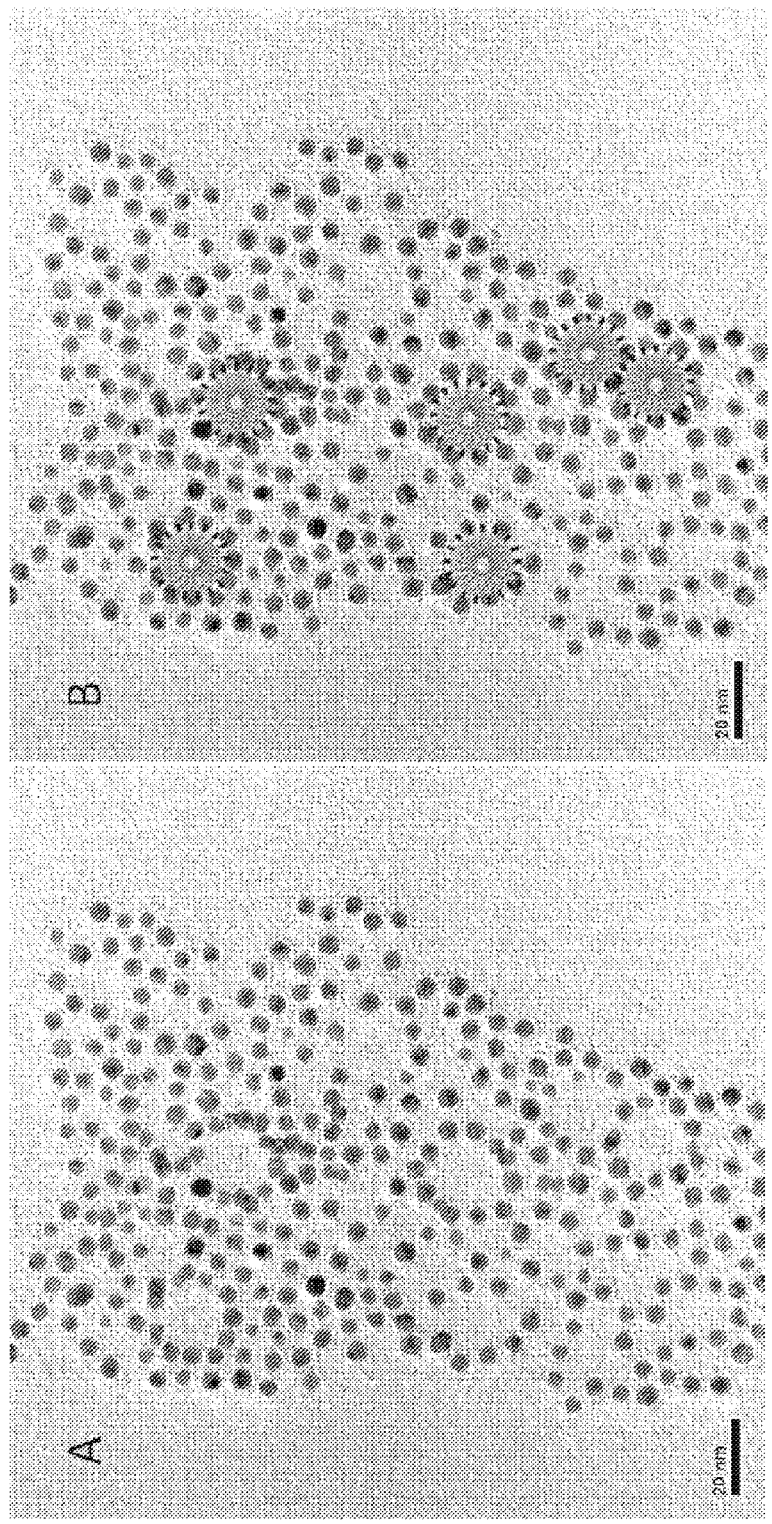
FIG. 8 shows transmission electron micrograph (TEM images) of His-TMV-CP disks-Au complexes. Samples were not stained.

FIG. 8 shows transmission electron micrograph (TEM images) of His-TMV-CP disks-Au complexes. Samples were not stained. FIG. 8A shows His-TMV-CP disk-Au complexes where the dark spots correspond to 5 nm gold. The disk-like structures correspond well with the expected 20 nm diameter for the His-TMV-CP disks. FIG. 8B uses the same image as FIG. 8A but with superimposed schematic images of the size and shape of the expected 20 nm disks. The contour generated by the Au binding to the disks matches well with the expected size and shape of the 20 nm disks.

Figure 9:
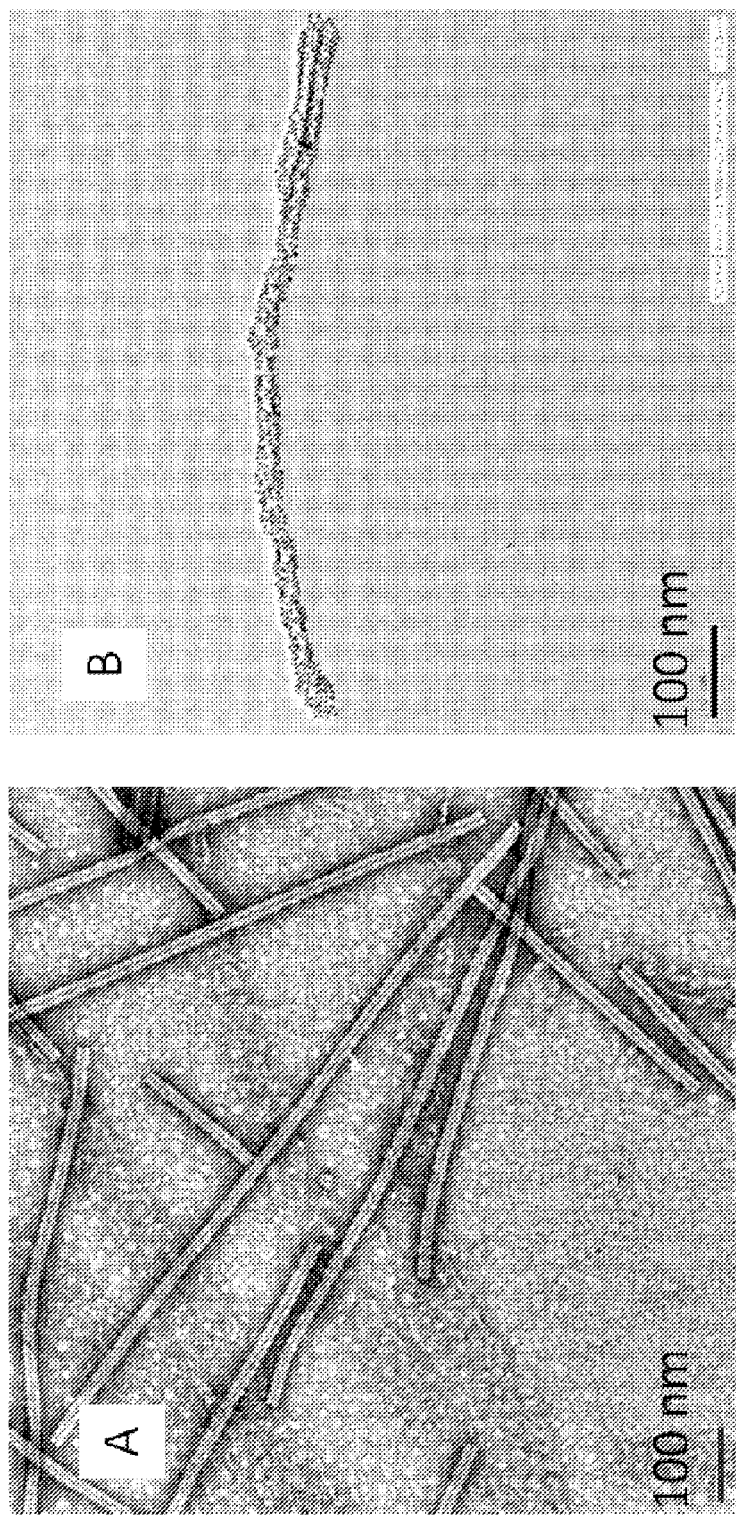
FIG. 9 shows TEM images of His-TMV-CP rods and rod-Au complexes.

FIG. 9 shows TEM images of His-TMV-CP rods and rod-Au complexes. FIG. 9A shows His-TMV-CP rods that were assembled in solution at 400 mM buffer concentration pH 5.0 and stained with uranyl acetate for visualization purposes. FIG. 9B shows His-TMV-CP rods after reaction with Ni-NTA-Nanogold and the sample was not stained; the dark spots correspond to 5 nm gold. This clearly establishes that the 5 nm gold attaches to the His-tag of the protein.

More Complex Structures and Applications of TMV Nanoresonators

More complex resonator structures can be assembled by utilizing the process described above. For example, the structures using His-TMV-CP metal nanoparticle decorated (metalized) disks can be expanded to include the concept of coupling two metalized TMV disks parallel with one another (as seen in FIG. 1) to create optically broad band circuit elements in an ABBA configuration (dual plasmonic ring TMV resonators) with the A sides of the coupled structure containing the metal nanoparticles. Further modification to the metal nanoparticles composing an A side can be accomplished by partial or complete nanoparticle attachment using plating techniques. The coupled ABBA configuration adds capacitance to the structure increasing the magnitude of the response and the spectral location of the response from the single disk resonator. Adjusting the spacing between the A layers containing the metal nanoparticles is a mechanism to further adjust the capacitance. By utilizing the random nature of the location of gaps between metal nanoparticles in the coupled plasmonic ring resonator system, which will shift the location of the optical resonance of the composite structure, an ensemble of these ABBA type resonators is expected produce a broad band optical (electric and magnetic) response. The magnitude of the optical response of an ensemble can be increased by increasing the density of the ABBA structures composing the ensemble, noting that the volume of an ABBA structure responsible for the response is approximately 25,000 times smaller than the volume of the wavelength of light at 500 nm, many such resonators can be placed within small well defined regions within a device.

Switching and/or tuning of the electronic and magnetic response of the structures should be possible by the addition of one or more semiconductor nanoparticles to the decorated TMV nanoparticle disks. Application of a secondary (external) source of excitation to the semiconductor nanoparticle(s) can be used to change the number of electrons within the semiconductor nanoparticle(s), thereby modifying the permittivity and permeability within a ring, changing the spectral resonant response of the ring and coupled structures described above. The amount of secondary excitation, such as by the use of the change in intensity of a laser tuned to an above bandgap semiconductor nanoparticle absorption band, can be used for switching on or off structures, or to provide change to the resonant properties of the structures, in real time (psec response) to actively tune the response. Semiconductor nanoparticle excitation can also be used to modify the capacitance of ABBA structures, further tuning the resonant properties of an individual ABBA structure and/or that of an ensemble device. Optical gain can be induced by the addition of fluorophores (dyes, nanoparticles) to an element or the ensemble, resonant with the optical response.

Structures can be excited by a variety of sources, including but not limited to natural light, laser light, and an electric field.

The utilization of protein-based nanostructures for the synthesis of disk- and rod-like structures offers the possibility of positioning control of inorganic elements at discrete sizes. This approach offers the advantage over the use of synthetic polymers of providing a unique molecular size as dictated by the encoded genes in designed clones. Protein production by means of *E. coli* fermentations offers the advantage of scalability, fast production, low cost, and low toxicity.

All publications mentioned herein are hereby incorporated by reference for the purpose of disclosing and describing the particular materials and methodologies for which the reference was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A protein structure comprising:
a plurality of tobacco mosaic virus coat proteins genetically modified to incorporate polyhistidine and in the form of protein disks of 18 nm diameter, configured as dual plasmonic ring resonators.

2. The protein structure of claim 1, wherein said polyhistidine is at a C-terminal end of said genetically modified tobacco mosaic virus coat protein.

3. The protein structure of claim 1, wherein the proteins are bound to a metal thereby forming metal-decorated disks of 20 to 30 nm diameter.

4. The protein structure of claim 3, wherein said metal comprises gold nanoparticles and/or silver nanoparticles.

5. The protein structure of claim 1:
(a) further comprising semiconductor nanoparticles;
(b) wherein a distance between said dual plasmonic ring resonators is adjusted to achieve a desired tuning; or both (a) and (b).

6. The protein structure of claim 5, wherein said metal comprises gold nanoparticles and/or silver nanoparticles.

7. A protein structure comprising:
a plurality of tobacco mosaic virus coat protein disks of 18 nm diameter and bound to a metal in the form of metal-decorated disks of 20 to 30 nm diameter, configured as dual plasmonic ring resonators.

8. The protein structure of claim 7:
(a) further comprising semiconductor nanoparticles;
(b) wherein a distance between said dual plasmonic ring resonators is adjusted to achieve a desired tuning; or both (a) and (b).

9. A method of obtaining metal nanoparticle decorated disks, the method comprising:
assembling a genetically modified tobacco mosaic virus coat protein incorporating polyhistidine into disks, and coating the disks with metal nanoparticles to obtain metal nanoparticle decorated disks of 20 to 30 nm diameter.

10. The method of claim 9, wherein said metal nanoparticles are gold nanoparticles and/or silver nanoparticles.

11. The method of claim 9, further comprising forming said metal nanoparticle decorated disks into dual plasmonic ring resonators.

12. The method of claim 11, wherein said dual plasmonic ring resonators are tuned to respond to:
(a) a laser tuned to an above bandgap semiconductor nanoparticle absorption band; or
(b) an electric field tuned to an above bandgap semiconductor nanoparticle energy band.

13. The method of claim 9, wherein a distance between said dual plasmonic ring resonators is adjusted to achieve a desired tuning.

14. The method of claim 13, further comprising adding a semiconductor nanoparticle to said nanoparticle decorated disks, thereby switching and/or tuning an electronic and magnetic response of the dual plasmonic ring resonators.

15. The method of claim 9, further comprising incorporating said dual plasmonic ring resonators into:
(a) a metamaterial composite with permeability less than one, or (b) a metamaterial composite with permeability less than zero.

16. The method of claim 9, further comprising incorporating said dual plasmonic ring resonators into a metamaterial composite with a negative index of refraction.

* * * * *

SEQUENCE LISTING

<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: primer

<400> SEQUENCE: 1
gattcgtttt acatatgtct tacagtatca ctac         34

<210> SEQ ID NO 2
<211> LENGTH: 54
<212> TYPE: DNA
<213> ORGANISM: Artificial Sequence
<220> FEATURE:
<223> OTHER INFORMATION: primer

<400> SEQUENCE: 2
tagtaccatg gtcattagtg atggtgatgg tgatgagttg caggaccaga ggtc         54

<210> SEQ ID NO 3
<211> LENGTH: 159
<212> TYPE: PRT
<213> ORGANISM: Artificial Sequence
<220> FEATURE:
<223> OTHER INFORMATION: synthetic construct

<400> SEQUENCE: 3

Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Gly Pro Ala Thr
145                 150                 155

<210> SEQ ID NO 4
<211> LENGTH: 170
<212> TYPE: PRT
<213> ORGANISM: Artificial Sequence
<220> FEATURE:
<223> OTHER INFORMATION: synthetic construct

<400> SEQUENCE: 4

Glu Gly Asp Ile His Met Ser Tyr Ser Ile Thr Thr Pro Ser Gln Phe
1               5                   10                  15

```
Val Phe Leu Ser Ser Ala Trp Ala Asp Pro Ile Glu Leu Ile Asn Leu
            20                  25                  30

Cys Thr Asn Ala Leu Gly Asn Gln Phe Gln Thr Gln Gln Ala Arg Thr
            35                  40                  45

Val Val Gln Arg Gln Phe Ser Glu Val Trp Lys Pro Ser Pro Gln Val
50                  55                  60

Thr Val Arg Phe Pro Asp Ser Asp Phe Lys Val Tyr Arg Tyr Asn Ala
65                  70                  75                  80

Val Leu Asp Pro Leu Val Thr Ala Leu Leu Gly Ala Phe Asp Thr Arg
                85                  90                  95

Asn Arg Ile Ile Glu Val Glu Asn Gln Ala Asn Pro Thr Thr Ala Glu
                100                 105                 110

Thr Leu Asp Ala Thr Arg Arg Val Asp Asp Ala Thr Val Ala Ile Arg
                115                 120                 125

Ser Ala Ile Asn Asn Leu Ile Val Glu Leu Ile Arg Gly Thr Gly Ser
            130                 135                 140

Tyr Asn Arg Ser Ser Phe Glu Ser Ser Ser Gly Leu Val Trp Thr Ser
145                 150                 155                 160

Gly Pro Ala Thr His His His His His His
                165                 170

<210> SEQ ID NO 5
<211> LENGTH: 170
<212> TYPE: PRT
<213> ORGANISM: Artificial Sequence
<220> FEATURE:
<223> OTHER INFORMATION: synthetic construct

<400> SEQUENCE: 5

Glu Gly Asp Ile His Met Ser Tyr Ser Ile Thr Thr Pro Ser Gln Phe
1               5                   10                  15

Val Phe Leu Ser Ser Ala Trp Ala Asp Pro Ile Glu Leu Ile Asn Leu
            20                  25                  30

Cys Thr Asn Ala Leu Gly Asn Gln Phe Gln Thr Gln Gln Ala Arg Thr
            35                  40                  45

Val Val Gln Arg Gln Phe Ser Glu Val Trp Lys Pro Ser Pro Gln Val
50                  55                  60

Thr Val Arg Phe Pro Asp Ser Asp Phe Lys Val Tyr Arg Tyr Asn Ala
65                  70                  75                  80

Val Leu Asp Pro Leu Val Thr Ala Leu Leu Gly Ala Phe Asp Thr Arg
                85                  90                  95

Asn Arg Ile Ile Glu Val Glu Asn Gln Ala Asn Pro Thr Thr Ala Glu
                100                 105                 110

Thr Leu Asp Ala Thr Arg Arg Val Asp Asp Ala Thr Val Ala Ile Arg
                115                 120                 125

Ser Ala Ile Asn Asn Leu Ile Val Glu Leu Ile Arg Gly Thr Gly Ser
            130                 135                 140

Cys Asn Arg Ser Ser Phe Glu Ser Ser Ser Gly Leu Val Trp Thr Ser
145                 150                 155                 160

Gly Pro Ala Thr His His His His His His
                165                 170
```